(12) United States Patent
Yamagami et al.

(10) Patent No.: US 6,937,691 B2
(45) Date of Patent: *Aug. 30, 2005

(54) X-RAY FLUORESCENCE SPECTROMETRIC SYSTEM AND A PROGRAM FOR USE THEREIN

(75) Inventors: Motoyuki Yamagami, Takatsuki (JP); Akihiro Ikeshita, Takatsuki (JP)

(73) Assignee: Rigaku Industrial Corporation, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/234,321

(22) Filed: Sep. 5, 2002

(65) Prior Publication Data

US 2003/0043963 A1 Mar. 6, 2003

(30) Foreign Application Priority Data

Sep. 6, 2001 (JP) .................................. 2001-270604

(51) Int. Cl.[7] ....................... G01N 23/223; B05C 11/02; B08B 3/04
(52) U.S. Cl. ........................ 378/45; 118/52; 118/663; 118/719; 134/1.3; 134/33; 134/34
(58) Field of Search ........................ 378/44, 45; 118/52, 118/663, 719; 134/1.3, 33, 34

(56) References Cited

U.S. PATENT DOCUMENTS

| | | | | |
|---|---|---|---|---|
| 5,395,446 A | * | 3/1995 | Kageyama et al. | 118/52 |
| 5,527,707 A | * | 6/1996 | Fukazawa | 436/72 |
| 5,742,658 A | * | 4/1998 | Tiffin et al. | 378/44 |
| 5,826,129 A | * | 10/1998 | Hasebe et al. | 396/611 |
| 5,916,824 A | * | 6/1999 | Mayuzumi et al. | 438/753 |
| 6,043,486 A | * | 3/2000 | Hossain | 250/252.1 |
| 6,053,984 A | * | 4/2000 | Petvai et al. | 134/3 |
| 6,164,133 A | * | 12/2000 | Watanabe | 73/432.1 |
| 6,173,036 B1 | * | 1/2001 | Hossain et al. | 378/45 |
| 6,174,740 B1 | * | 1/2001 | Ohta et al. | 438/14 |
| 6,182,675 B1 | * | 2/2001 | Naka et al. | 134/61 |
| 6,381,303 B1 | * | 4/2002 | Vu et al. | 378/46 |
| 6,611,577 B1 | * | 8/2003 | Yamagami | 378/48 |
| 2003/0084926 A1 | * | 5/2003 | Watanabe | 134/33 |

FOREIGN PATENT DOCUMENTS

JP          09-072836 A          3/1997

OTHER PUBLICATIONS

C. Neumann and P. Eichinger, Ultra–trace analysis of metallic contaminations on silicon wafer surfaces by vapor phase decomposition/total reflection X–Ray fluorescene (VPD/TXRF), Spectrochimica Acta, vol. 46B, No. 10, 1991.*

* cited by examiner

Primary Examiner—Allen C. Ho
(74) Attorney, Agent, or Firm—Birch, Stewart, Kolasch & Birch, LLP

(57) ABSTRACT

An X-ray fluorescence spectrometric system includes a sample pre-treatment apparatus 10 for retaining on a surface of a substrate a substance to be measured that is found on the surface of the substrate, after such substance has been dissolved and subsequently dried, an X-ray fluorescence spectrometer 40, and a transport apparatus 50 for transporting the substrate from the sample pre-treatment apparatus towards the X-ray fluorescence spectrometer, which system as a whole is easy to operate. This spectrometric system also includes a control apparatus 50 for controlling the sample pre-treatment apparatus 10, the X-ray fluorescence spectrometer 40 and the transport apparatus 50 in a totalized fashion.

9 Claims, 5 Drawing Sheets

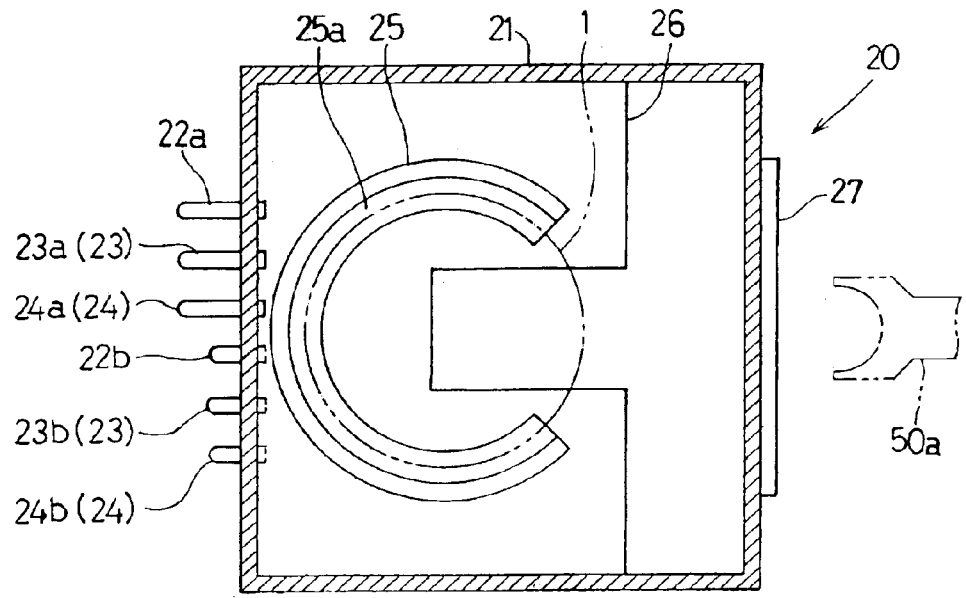
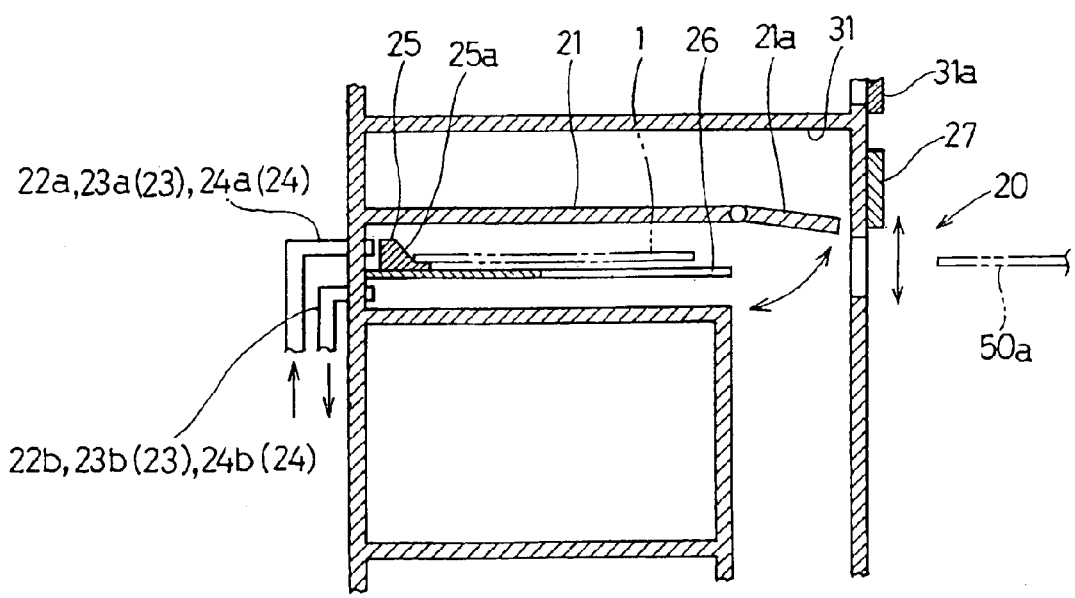

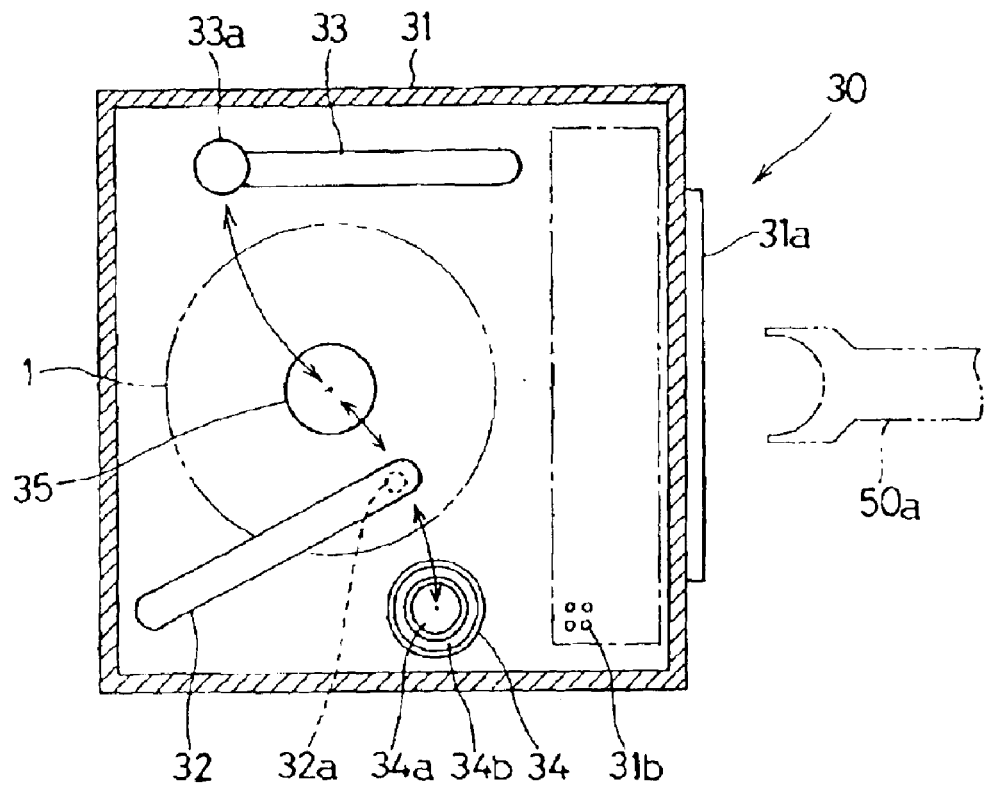
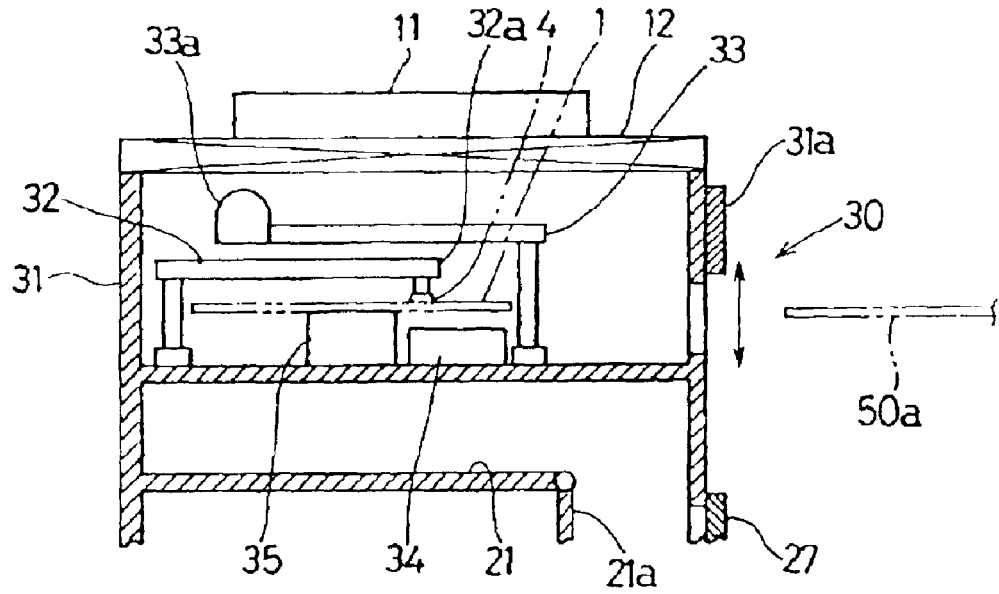

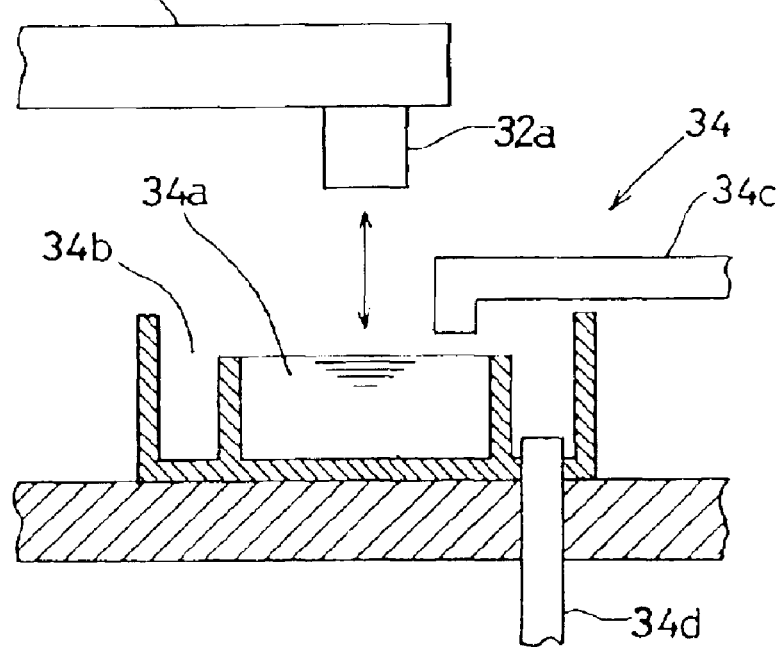
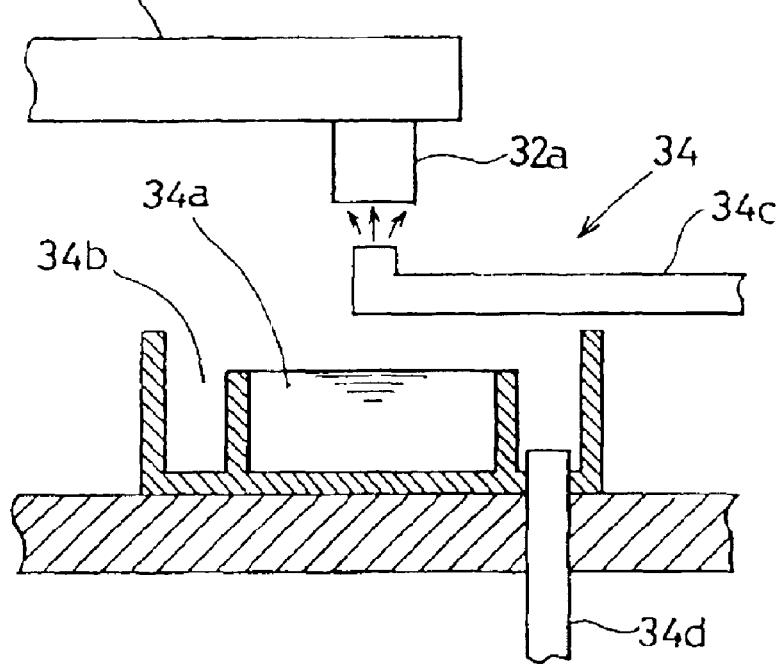

X-RAY FLUORESCENCE SPECTROMETRIC SYSTEM AND A PROGRAM FOR USE THEREIN

BACKGROUND OF THE INVENTION

1. Field of the Invention

The present invention relates to an X-ray fluorescence spectrometric system of a type including a sample pre-treatment apparatus for retaining on a surface of a substrate a substance to be measured that is found on the surface of the substrate, after such substance has been dissolved and subsequently dried, an X-ray fluorescence spectrometer for measuring intensities of fluorescent X-rays emitted from the substance to be measured upon irradiation with primary X-rays, and a transport apparatus for transporting the substrate from the sample pre-treatment apparatus towards the X-ray fluorescence spectrometer.

2. Description of the Prior Art

There is known a system in which in order for a fluorescent X-ray analysis to be performed on a small quantity of contaminants deposited on a semiconductor substrate, the substrate is transported from a sample pre-treatment apparatus to an X-ray fluorescence spectrometer by means of a transport apparatus such as, for example, a manipulator or robotic arm. An example of such system is disclosed in, for example, the Japanese Patent Application No. 2001-077917 filed Mar. 19, 2001. In this prior art, a heating process in the sample pre-treatment apparatus is controlled by a control means.

However, the conventional system is not equipped with a control apparatus designed to control the sample pre-treatment apparatus, the X-ray fluorescence spectrometer and the transport apparatus in a totalized fashion and those apparatuses are individually controlled in different environments (software). Accordingly, the conventional system as a whole is incapable of being controlled easily.

SUMMARY OF THE INVENTION

The present invention has been devised with a view to substantially eliminating the inconveniences inherent in the conventional system discussed above and is intended to provide an X-ray fluorescence spectrometric system of a type including a sample pre-treatment apparatus for retaining on a surface of a substrate a substance to be measured that is found on the surface of the substrate, after such substance has been dissolved and subsequently dried, an X-ray fluorescence spectrometer for measuring intensities of fluorescent X-rays emitted from the substance to be measured upon irradiation with primary X-rays, and a transport apparatus for transporting the substrate from the sample pre-treatment apparatus towards the X-ray fluorescence spectrometer, which system as a whole is easy to operate.

Another important object of the present invention is to provide a software program that can be used in association with the X-ray fluorescence spectrometric system of the type discussed above.

In order to accomplish the foregoing objects of the present invention, there is provided an X-ray fluorescence spectrometric system includes a vapor phase decomposition apparatus, a sample recovery apparatus, an X-ray fluorescence spectrometer, a transport apparatus and a control apparatus as will be described in detail later. It is to be noted that the vapor phase decomposition apparatus and the sample recovery apparatus, both referred to above, altogether constitute a sample pre-treatment apparatus.

The vapor phase decomposition apparatus is operable to retain on a surface of a substrate a substance to be measured that is found on the surface of the substrate or a substance to be measured that is found on a surface of a film formed on the surface of the substrate or within the film, after such substance has been dissolved by a reactive gas and has subsequently been dried, in a decomposing chamber. The sample recovery apparatus is operable to drop a solution on the substrate having the surface on which the substance to be measures exists, to move the solution on the substrate surface while being retained by a retainer, and to retain the substance to be measured on the substrate surface after having been recovered in the solution and then dried, in a recovery chamber that is disposed above the decomposing chamber. The X-ray fluorescence spectrometer is operable to measure intensities of fluorescent X-rays emitted from the substance to be measured that is retained on the substrate by the vapor phase decomposition apparatus or the sample recovery apparatus, when such substance is irradiated by primary X-rays. The transport apparatus is operable to transport the substrate from the decomposing chamber towards the X-ray fluorescence spectrometer, to transport the substrate from the decomposing chamber towards the recovery chamber and to transport the substrate from the recovery chamber towards the X-ray fluorescence spectrometer. The control apparatus controls the vapor phase decomposition apparatus, the sample recovery apparatus, the X-ray fluorescence spectrometer and the transport apparatus.

According to the present invention, since the X-ray fluorescence spectrometric system is provided with the control apparatus capable of controlling all of those apparatuses and the spectrometer in a totalized fashion, the system as a whole can be easy to operate.

The present invention also provides an X-ray fluorescence spectrometric system similar to the previously described X-ray fluorescence spectrometric system, but differs therefrom in that the sample recovery apparatus is excluded from the sample pre-treatment apparatus. Even with this alternative X-ray fluorescence spectrometric system, since the control apparatus for controlling the various apparatuses and the spectrometer in a totalized fashion is employed, the system as a whole can be easy to operate.

The present invention furthermore provides an X-ray fluorescence spectrometric system similar to the first mentioned X-ray fluorescence spectrometric system, but differs therefrom in that the vapor phase decomposition apparatus is dispensed with. Even with this further alternative X-ray fluorescence spectrometric system, since the control apparatus for controlling the various apparatuses and the spectrometer in a totalized fashion is employed, the system as a whole can be easy to operate.

In one preferred embodiment of the present invention, the vapor phase decomposition apparatus includes a decomposing chamber cleansing means for flushing a cleansing liquid into the decomposing chamber to cleanse the latter. The use of the decomposing chamber cleansing means automates a cleansing operation of the decomposing chamber and, therefore, the operation of the system can be facilitated.

In one preferred embodiment of the present invention, the vapor phase decomposition apparatus includes a heating means for heating a gas to be introduced into the decomposing chamber. The use of the heating means in the vapor phase decomposition apparatus effectively facilitates analysis and drying of the substance to be measured within the decomposing chamber.

In one preferred embodiment of the present invention, the vapor phase decomposition apparatus includes a substrate support having a downwardly narrowed taper formed with an inner periphery thereof so that the substrate can be placed at a predetermined position within the decomposing chamber. With this structural feature, merely by positioning the substrate on the substrate support within the decomposing chamber, it can be properly positioned and, therefore, the next succeeding recovery and analysis can be performed accurately.

In a further preferred embodiment of the present invention, the sample recovery apparatus preferably includes a retainer cleansing means for cleansing the retainer with a cleansing liquid. The use of the retainer cleansing means allows the retainer to be automatically cleansed, making it possible to facilitate manipulation of the system.

In a still preferred embodiment of the present invention, the sample recovery apparatus preferably includes a rotary table for rotating the substrate in a horizontal plane when the substance to be measured that has been recovered in the solution is dried. The use of the rotary table is effective to prevent the substance to be measured from being disproportionately dried and, hence, spread on the substrate and, accordingly, an accurate analysis of the substance to be measured can be achieved.

According to a different aspect of the present invention, the present invention also provides a program enabling the control apparatus, included in the X-ray fluorescence spectrometric system discussed above, to perform one of VPD, VPT and TXRF modes, discussed below, according to a selection made by an operator. In the VPD mode, the transport apparatus is caused to transport the substrate from a predetermined delivery position towards the decomposing chamber. Subsequently, the vapor phase decomposition apparatus is caused to introduce the reactive gas into the decomposing chamber. Then, the transport apparatus is caused to transport the substrate towards the recovery chamber. Next, the sample recovery apparatus is caused to drop the solution onto the substrate. After it, the sample recovery apparatus is caused to move the dropped solution, while being retained by the retainer, along a surface of the substrate and then to recover the substance to be measured. Thereafter, the sample recovery apparatus is caused to dry the substance to be measured. Next, the transport apparatus is caused to transport the substrate towards the X-ray fluorescence spectrometer. Thereafter, the X-ray fluorescence spectrometer is caused to measure intensities of fluorescent X-rays emitted from the substance to be measured in response to irradiation thereof with primary X-rays. Thereafter, the transport apparatus is caused to transport the substrate back towards the delivery position.

In the VPT mode, in the first place, the transport apparatus is caused to transport the substrate from the predetermined delivery position towards the decomposing chamber. After it, the vapor phase decomposition apparatus is caused to introduce the reactive gas into the decomposing chamber. Then, the transport apparatus is caused to transport the substrate towards the X-ray fluorescence spectrometer. Thereafter, the X-ray fluorescence spectrometer is caused to measure intensities of fluorescent X-rays emitted from the substance to be measured in response to irradiation thereof with primary X-rays. Thereafter, the transport apparatus is caused to transport the substrate back towards the delivery position.

In the TXRF mode, in the first place, the transport apparatus is caused to transport the substrate from the predetermined delivery position towards the X-ray fluorescence spectrometer. After it, the X-ray fluorescence spectrometer is caused to measure intensities of fluorescent X-rays emitted from the substance to be measured in response to irradiation thereof with primary X-rays. Thereafter, the transport apparatus is caused to transport the substrate back towards the delivery position. With this program according to the present invention, the control apparatus can control the various apparatuses and the spectrometer in a totalized fashion and, therefore, the system as a whole can be easily operated.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 2A is a schematic plan view of a vapor phase decomposition apparatus employed in the spectrometric system;

FIG. 2B is a schematic front elevational view of the vapor phase decomposition apparatus shown in FIG. 2A;

FIG. 3A is a schematic plan view of a sample recovery apparatus employed in the spectrometric system;

FIG. 3B is a schematic front elevational view of the sample recovery apparatus shown in FIG. 3A;

FIG. 4A is a schematic front elevational view of a retainer cleansing means employed in the sample recovery apparatus of the spectrometric system, showing the manner in which a retainer is immersed in a cleansing liquid;

FIG. 4B is a schematic front elevational view of the retainer cleansing means, showing the manner in which the retainer is blown with a cleansing liquid.

DETAILED DESCRIPTION OF THE EMBODIMENT

Figure 1A:
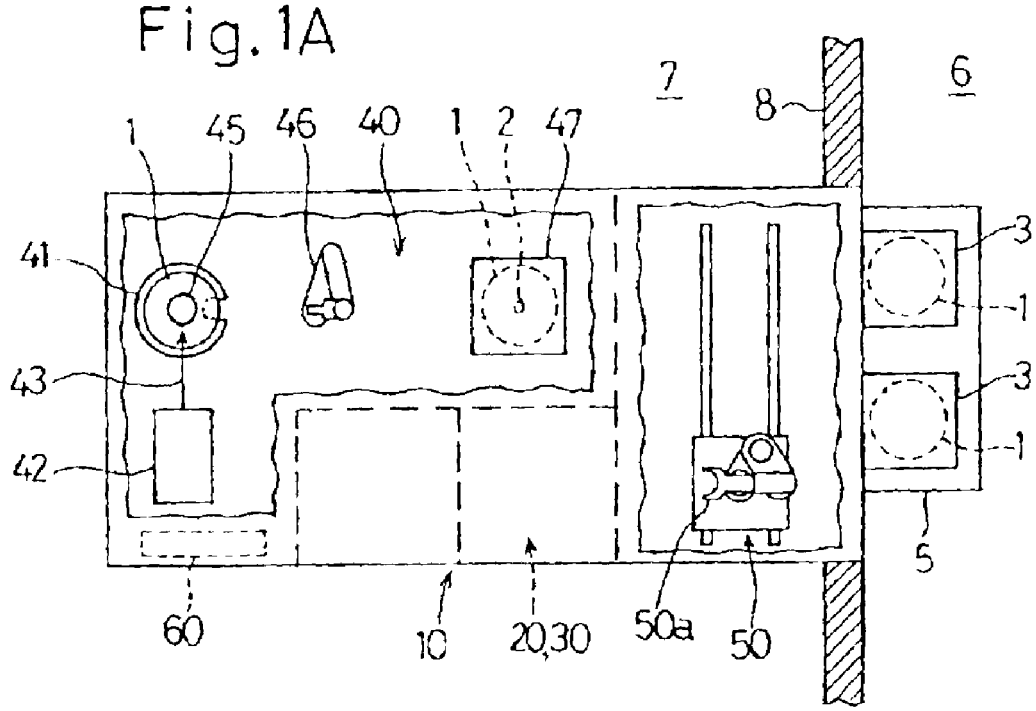
FIG. 1A is a schematic plan view, with portions cut out, of an X-ray fluorescence spectrometric system according to a preferred embodiment of the present invention.
Figure 1B:
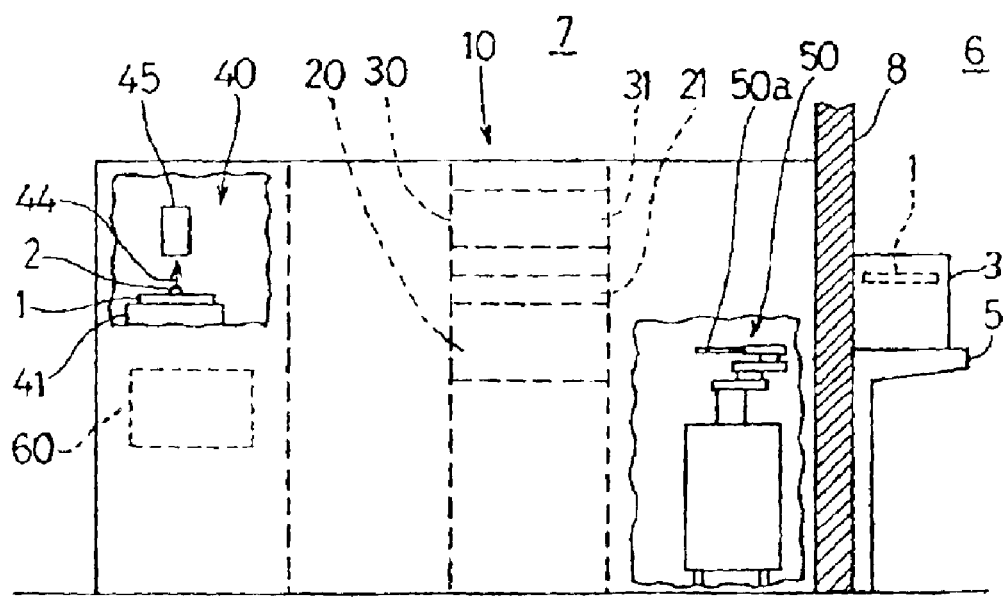
FIG. 1B is a schematic front elevational view, with portions cut out, of the X-ray fluorescence spectrometric system shown in FIG. 1A.

The structure of an X-ray fluorescence spectrometric system according to a preferred embodiment of the present invention will now be described. Referring first to FIGS. 1A and 1B, the X-ray fluorescence spectrometric system includes a sample pre-treatment apparatus 10 having a vapor phase decomposition apparatus 20 and a sample recovery apparatus 30, an X-ray fluorescence spectrometer 40 having an X-ray source 42 for projecting primary X-rays 43 towards a substance 2 to be measured, which is placed on a substrate 1 supported on a sample table 41, so as to irradiate the substance 2 to be measured and a detecting means 45 for measuring intensities of fluorescent X-rays 44 emitted from the substance 2 to be measured as it is excited by the primary X-rays 43, and a transport apparatus 50 for transporting the substrate 1 from the sample pre-treatment apparatus 10 towards the X-ray fluorescence spectrometer 40.

In the illustrated embodiment, the X-ray fluorescence spectrometer 40 employed is of a total reflection type in which the primary X-rays emitted from the X-ray source 42 impinge upon the sample at a minute angle of incidence. The X-ray source 42 employed therein includes an X-ray tube, a spectroscopic device element for monochromating and others. The detecting means 45 employs a SSD or the like. The X-ray fluorescence spectrometer 40 includes a transport means 46 such as a robotic arm or manipulator arm and operable to transport the substrate 1 between a cassette 47 within a delivery chamber and the sample table 41.

The transport apparatus 50 includes a transport body in the form of a robotic hand capable of moving forwards and rearwards along a guide rail. This transport apparatus 50 is capable of transporting the substrate 1, when the latter is mounted on a hand portion 50a, from a cassette 3 (a predetermined delivery position) mounted on a cassette support 5 of the spectrometric system towards a decomposing chamber 21 or a recovery chamber 31 of the sample pre-treatment apparatus 10, from the decomposing chamber 21 or the recovery chamber 31 towards the cassette 47 within the delivery chamber of the X-ray fluorescence spectrometer 40, and from the cassette 47 within the delivery chamber back towards the initial cassette 3 placed on the cassette support 5. The cassette support 5 is capable of supporting thereon a plurality of cassettes 3.

The spectrometric system is adapted to be installed so as to extend completely through a partition wall 8 separating between a clean room 6 where a semiconductor manufacturing apparatus or the like is installed, and an analyzing chamber 7 where the semiconductor substrate 1 manufactured in the clean room 6 is analyzed. Only the cassette support 5 is positioned within the clean room. Although not shown, a shutter is provided between the cassette 3 placed on the cassette support 5 and the transport apparatus 50.

The spectrometric system also includes a control apparatus 60 such as, for example, a computer, for controlling the sample pre-treatment apparatus 10, the X-ray fluorescence spectrometer 40, the transport apparatus 50 and the shutter disposed between the cassette 3 placed on the cassette support 5 and the transport apparatus 50, in a common environment (a software). This control apparatus 60 is disposed within, for example, the X-ray fluorescence spectrometer 40. Each of those apparatuses are aggregated together on a common support bench and are all housed within an integral housing.

Of the sample pre-treatment apparatus 10, the vapor phase decomposition apparatus 20 is operable to retain on a surface of the substrate the substance to be measured that is found on the surface of the substrate or the substance to be measured that is found on a surface of a film formed on the surface of the substrate or within the film, after such substance has been dissolved by a reactive gas and has subsequently been dried, in the decomposing chamber 21. The sample recovery apparatus 30 is operable to drop a solution on the substrate having the surface on which the substance to be measures exists, to move the solution on the substrate surface while being retained by a retainer, and to retain the substance to be measured on the substrate surface after having been recovered in the solution and then dried, in the recovery chamber 31 that is disposed above the decomposing chamber 21.

The details of the vapor phase decomposition apparatus 20 will be discussed. As shown in FIGS. 2A and 2B, the decomposing chamber 21 of the vapor phase decomposition apparatus 20 is in the form of a box made of, for example, polytetrafluoroethylene (PTFE, trademarked "Teflon") and includes a selectively opening and closing inner shutter 21a positioned on one side confronting the hand portion 50a of the transport apparatus 50. A selectively opening and closing outer shutter 27 is provided at an outer wall of the vapor phase decomposition apparatus 20 at a location spaced from the inner shutter 21a through a space in which a stream of air flowing from the recovery chamber 31 defined thereabove can flow downwards. A reactive gas such as, for example, hydrogen fluoride (or hydrofluoric acid) is introduced into the decomposing chamber 21 through a tubing 22a so that not only can an oxide film formed on the surface of the substrate 1 such as, for example, a silicon wafer be dissolved, but the substance to be measured such as a contaminant present on the surface of the film and/or within the film can be dissolved, with an unreacted gas being subsequently discharged through a tubing 22b. Where no film is formed on the surface of the substrate 1, the substance to be measured that is present on the surface of the substrate 1 is dissolved.

The vapor phase decomposition apparatus 20 includes a decomposing chamber cleansing means 23 for flushing an ultra pure water as a cleansing liquid into the decomposing chamber 21 to cleanse the decomposing chamber 21, that is, a cleansing liquid introducing tubing 23a and a discharge tubing 23b. The vapor phase decomposition apparatus 20 also includes a droplet drying means 24 for introducing a clean nitrogen as an inactive gas into the decomposing chamber 21 to purge the hydrogen fluoride and also to dry droplets deposited on the substrate 1, that is, a nitrogen introducing tubing 24a and a discharge tubing 24b. It is to be noted that for the droplet drying means, in place of or in addition to the flow of the inactive gas, the interior of the decomposing chamber may be evacuated to a substantial vacuum to dry the droplets on the substrate. In such case, evacuation and introduction of the inactive gas may be performed repeatedly.

Also, the vapor phase decomposition apparatus 20 includes a heating means 28 positioned at a lower area thereof for externally heating the tubings 22a and 24a for introducing hydrogen fluoride and nitrogen, respectively, into the decomposing chamber 21. This heating means 28 is, in the illustrated embodiment employed in the form of a constant temperature bath having a heater built therein. It is to be noted that the heating of the tubings 22a and 24a may be carried out by a heater or the like built inside each of those tubings or by a heater for heating a trap disposed on a portion of each of those tubings. Also, as shown in FIG. 2, in order for the substrate 1 to be mounted at a predetermined position within the decomposing chamber 21, the vapor phase decomposition apparatus 20 includes a substrate support 25 having its inner periphery tapered as downwardly as at 25a to a narrow width. In other words, the substrate support 25 is in the form of a ring having a portion thereof depleted to avoid any possible interference with the hand portion 50a of the transport apparatus and has its inner periphery formed with a tapered face 25a that represents a downwardly oriented conical surface and is fixed within the decomposing chamber 21 by means of a partition plate 26.

The details of the sample recovery apparatus 30 will now be described. As shown in FIGS. 3A and 3B, the recovery chamber 31 of the sample recovery apparatus 30 is in the form of a box made of polyvinyl chloride (PVC) and is provided with a fan 11 and a filter 12 both mounted atop the recovery chamber 31. This recovery chamber 31 is disposed above the decomposing chamber 21 and is provided with a selectively opening and closing shutter 31a positioned so as to confront the hand portion 50a of the transport apparatus. The recovery chamber 31 has a bottom plate formed with a plurality of punched holes 31b defined at an area adjacent the shutter 31a (encompassed within the single-dotted chain line in FIG. 3A) so that a stream of clean air introduced into the recovery chamber 31 through the filter 12 by means of the fan 11 can flow downwardly and outwardly of the inner shutter 21a of the decomposing chamber 21. The sample recovery apparatus 30 includes a recovering liquid moving means 32, a recovered liquid drying means 33, a retainer cleansing means 34 and a rotary table 35, all of which will subsequently be described.

The recovering liquid moving means 32 is in the form of an arm operable to move a retainer 32a, positioned downwardly of a free end of such arm, above the substrate 1 mounted on the rotary table 35 arcuately between an outside of the substrate 1 and a center portion thereof and also operable to move the retainer 32a up and down. The retainer 32a is in the form of a nozzle made of, for example, PTFE, to which a hydrofluoric acid solution 4 from a tank positioned further downwardly of the decomposing chamber 21 is supplied. The rotary table 35 is used to support thereon and rotate the substrate 1 in a horizontal plane. In other words, the sample recovery apparatus 30 is so designed and so configured that the hydrofluoric acid solution 4 of a quantity, for example, 100 microlitter that has been dropped from the retainer 32a onto an outer peripheral portion of the substrate 1 can be, while the substrate 1 is being rotated, moved centripetally towards the center of the substrate 1, while the quantity of the hydrofluoric acid solution is sandwiched between the retainer 32a and the substrate 1, so as to recover the substance to be measured that is present on the surface of the substrate 1.

The recovered liquid drying means 33 is in the form of an arm operable to move a lamp 33a, provided at a free end of such arm so as to be oriented downwardly, above the substrate I arcuately between an outside of the substrate 1 and the center thereof. In other words, the sample recovery apparatus 30 is operable to move the lamp 33a towards a position immediately above the center of the substrate 1 and then to heat the solution 4, which has recovered the substance to be measured, to thereby dry it. Even during this drying, the substrate 1 is rotated together with the rotary table 35 in the horizontal plane.

The retainer cleansing means 34 is of a structure including as shown in FIG. 4A a vessel including a cylindrical inner bath 34a having a bottom plate and an outer bath 34b of a generally ring shape positioned radially outwardly of the inner bath 34a. This vessel is provided with a supply tubing 34c positioned above the inner bath 34a for supplying a cleansing liquid in the form of an ultra pure water into the inner bath 34a so as to allow the cleansing liquid to overflow the inner bath 34a, and also with a discharge tubing 34d fluid-connected with the bottom of the outer bath 34b for draining the cleansing liquid that has flown over the inner bath 34a. Referring to FIG. 3, the sample recovery apparatus 30 is so designed and so configured that the retainer 32a can be moved by the recovering liquid moving means 32 from the outside of the substrate 1 towards a position immediately above the inner bath 34a of the retainer cleansing means 34, that is positioned further outside the outer periphery of the substrate 1, and can then be moved up and down as shown in FIG. 4A. In other words, at least a lower end portion of the retainer 32a is immersed into the cleansing liquid to clean it. The supply tubing 34c is preferably supported in a non-contact fashion with and, hence, separated from the cleansing liquid within the inner bath 34a as shown so that a contaminant contained in the cleansing liquid within the inner bath 34a, which has already been used for cleansing, will not enter the supply tubing 34c. It is to be noted that the cleansing may be effected by blowing the cleansing liquid towards the retainer 32a. In this case, as shown in FIG. 4B, the supply tubing 34c has to be positioned with its open end oriented upwardly so that the cleansing liquid can be blown from below towards the retainer 32a.

In the description that follows, a program employed in the control apparatus 60, shown in FIG. 1, of the X-ray fluorescence spectrometric system of the present invention will be discussed. This program is used to cause the control apparatus 60 to execute one of the following VPD, VPT and TXRF modes according to a selection made by an operator. In the VPD mode, the transport apparatus 50 is caused to transport the substrate 1 from the predetermined delivery position towards the decomposing chamber 21. Subsequently, the vapor phase decomposition apparatus 20 is caused to introduce the reactive gas into the decomposing chamber 21, which gas is purged out of the decomposing chamber 21 a predetermined time thereafter. Then, the transport apparatus 50 is caused to transport the substrate 1 towards the recovery chamber 31. Next, the sample recovery apparatus 30 shown in FIG. 3 is caused to drop the solution 4 onto the substrate 1. After it, the sample recovery apparatus 30 is caused to move the dropped solution 4, while being retained by the retainer 32a, along a surface of the substrate 1 and then to recover the substance to be measured. Thereafter, the sample recovery apparatus 30 is caused to dry the substance to be measured. Next, the transport apparatus 50 shown in FIG. 1 is caused to transport the substrate 1 towards the X-ray fluorescence spectrometer 40. Thereafter, the X-ray fluorescence spectrometer 40 is caused to measure intensities of fluorescent X-rays 44 emitted from the substance to be measured in response to irradiation thereof with primary X-rays 43. Thereafter, the transport apparatus 50 is caused to transport the substrate 1 back towards the delivery position.

In the VPT mode, the transport apparatus 50 is in the first place caused to transport the substrate 1 from the predetermined delivery position towards the decomposing chamber 21. After it, the vapor phase decomposition apparatus 20 is caused to introduce the reactive gas into the decomposing chamber 21, which gas is purged out of the decomposing chamber 21 a predetermined time thereafter. Then, the transport apparatus 50 is caused to transport the substrate 1 towards the X-ray fluorescence spectrometer 40. Thereafter, the X-ray fluorescence spectrometer 40 is caused to measure intensities of fluorescent X-rays 44 emitted from the substance to be measured in response to irradiation thereof with primary X-rays 43. Thereafter, the transport apparatus 50 is caused to transport the substrate 1 back towards the delivery position.

In the TXRF mode, the transport apparatus 50 is in the first place caused to transport the substrate 1 from the predetermined delivery position towards the X-ray fluorescence spectrometer 40. After it, the X-ray fluorescence spectrometer 40 is caused to measure intensities of fluorescent X-rays 44 emitted from the substance to be measured in response to irradiation thereof with primary X-rays 43. Thereafter, the transport apparatus 50 is caused to transport the substrate 1 back towards the delivery position.

The operation of the X-ray fluorescence spectrometric system will now be described. Within the clean room shown in FIG. 1, when the cassette 3 accommodating therein the substrates 1, for example, silicone wafers containing a contaminant to be analyzed are mounted on the cassette support 5 and an instruction to preprocess and analyze the substrate 1 within the cassette 3 (the predetermined delivery position) under a predetermined condition is subsequently inputted from an input means (not shown) to the control apparatus 60, the various apparatus and the spectrometer of the spectrometric system can be controlled to perform as follows. Since the preprocessing and analyzing conditions can be set for each substrate 1 by means of the input means (not shown) while the operator looks at a display means (not shown) of the control apparatus 60 and the sample pretreatment apparatus 10, the X-ray fluorescence spectrometer 40 and the transport apparatus 60 can be controlled in a common environment, the system as a whole is easy to operate.

In the spectrometric system of the present invention, as the preprocessing and analyzing conditions, three modes, i.e., VPD, VPT and TXRF modes are available and the operation of the spectrometric system under the VPD (vapor phase decomposition) mode will first be described. At the outset, the transport apparatus 50 transports the substrate 1 towards the decomposing chamber 21 and places it on the substrate support 25 as shown in FIG. 2. At the time of delivery, the shutters 21a and 27 of the vapor phase decomposition chamber 20 are automatically opened. Since the substrate support 25 has its inner periphery formed with the downwardly narrowed taper 25a, even though the substrate 1 is somewhat displaced from a predetermined position on the hand portion 50a, mere placement of the substrate 1 on the substrate support 25 is effective to allow the substrate 1 to be slipped onto the substrate support 25 by the effect of its own weight and, hence, to be properly positioned and, accordingly, the subsequent recovery and analysis can be accurately performed.

Figure 5:
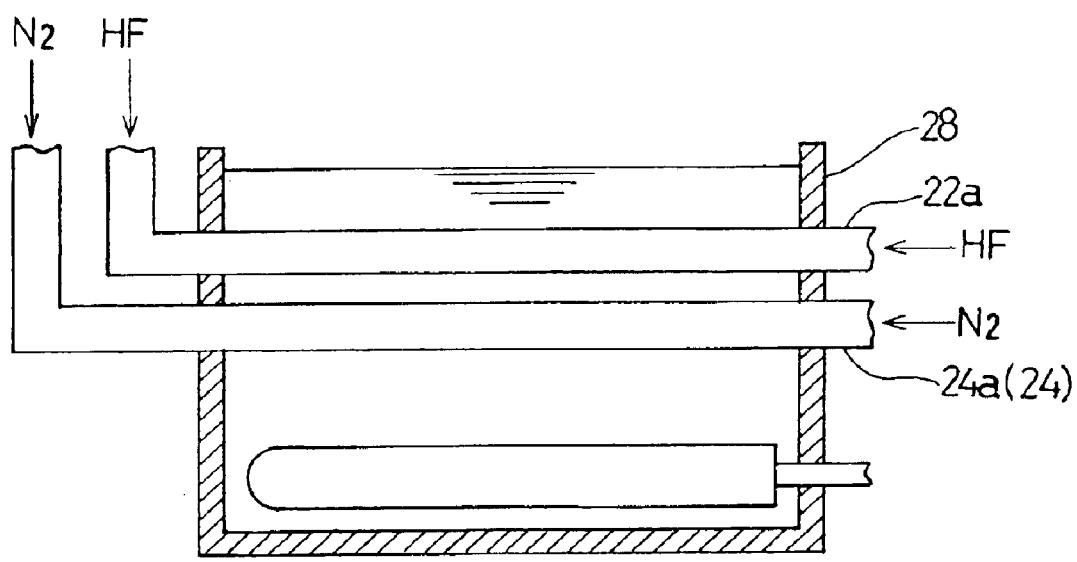
FIG. 5 is a schematic front elevational view of a heating means employed in the vapor phase decomposition apparatus of the spectrometric system.

The hydrogen fluoride is then introduced through the tubing 22a into the sealed decomposing chamber 21 with the shutters 21a and 27 closed, to thereby dissolve the oxide film formed on the surface of the substrate 1 and also to dissolve the substance to be measured such as the contaminant present on the surface of the film and/or within the film, and the hydrogen fluoride is subsequently discharged through the tubing 22b. Where no film is formed on the surface of the substrate 1, the substance to be measured that is present on the surface of the substrate 1 is dissolved. At the time of introduction of the hydrogen fluoride, it is preferred that a valve on the discharge tubing 22b is opened prior to opening of a valve on the introducing tubing 22a, but this is not always essential, and the reverse or the synchronous opening may be acceptable. The hydrogen fluoride introduced into the decomposing chamber 21 is heated by the heating means 28 exteriorly through the tubing 22a as shown in FIG. 5 and, therefore, decomposition of the oxide film within the decomposing chamber 21 can properly and quickly take place. The vapor phase decomposition by this hydrogen fluoride is performed for, for example, 10 minutes which can be set.

After a predetermined length of time during which the vapor phase decomposition is performed, nitrogen is allowed to flow by the droplet drying means 24 while the decomposing chamber 21 is evacuated, resulting in purge of the hydrogen fluoride and, at the same time, the droplets formed on the substrate 1 can be dried. In this way, during the subsequent transport, the hand portion 50a of the transport apparatus will not be brought into contact with the droplets and will not therefore be corroded and, therefore, there is no possibility that the transport will be inaccurate, which would otherwise occur when the substrate 1 undergoes slippage on the hand portion 50a. Also, there is no possibility that the hydrogen fluoride may constitute a cause of corrosion which would occur when it flow into the transport apparatus 50 and/or the X-ray fluorescence spectrometer 40 (FIG. 1). Even in this situation, since the nitrogen is heated by the heating means 20 without being contaminated as shown in FIG. 5, drying of the droplets can be properly and quickly preformed within the decomposing chamber 21. Also, the decomposing chamber 21 is routinely cleansed with the ultra pure water by the decomposing chamber cleansing means 23. In this way, since the cleansing of the interior of the decomposing chamber 21 as well is automated, the system can be further easily operated.

In the next place, the transport apparatus 50 transports the substrate 1 towards the recovery chamber 3 shown in FIG. 3 so that the substrate 1 can be placed on the rotary table 35 with its center aligned with the center of rotation of the rotary table 35. At the time of this transport, the shutters 21a, 27 and 31a of the vapor phase decomposition apparatus 20 and the sample recovery apparatus 30 are automatically opened and closed. In this way, since transport of the substrate 1 from the decomposing chamber 21 towards the recovery chamber 31 is also performed by the transport apparatus 50, any possible contamination resulting from a manual intervention can be avoided and an accurate analysis is therefore possible. Thereafter, the sample recovery apparatus 30 moves the hydrofluoric acid solution 4, which has been dropped from the retainer 32a onto an outer peripheral portion of the substrate 1, towards the center of the substrate 1 while the substrate 1 is rotated and the hydrofluoric acid solution 4 is retained by the retainer 32a to thereby recover the substance to be measured present on the surface of the substrate 1 (i.e., the substance to be measured that is retained by the vapor phase decomposition apparatus 20 on the surface of the substrate 1). The position at which the hydrofluoric acid solution 4 is dropped and the path of movement of the retainer 32a during the recovery process may not be limited to those described above and variants thereof can be contemplated. After the recovery, the retainer 32a is elevated and moved to a position above the inner bath 34a of the retainer cleansing means 34 and is then immersed into the cleansing liquid to cleanse it. In this way, cleansing of the retainer 32a is also automated and, accordingly, the system can be further easy to operate.

Then, the sample recovery apparatus 30 move the lamp 33a to a position immediately above the center of the substrate 1 to heat the solution 4, which has recovered the substance to be measured, to thereby dry the substance to be measured. Even during this drying, the substrate 1 is rotated in the horizontal plane together with the rotary table 35. Accordingly, since there is no possibility that the substance to be measured may be disproportionately dried and spread, a further accurate analysis is possible. Also, since the recovery chamber 31 is arranged above the decomposing chamber 21 and a stream of clean air flowing into the recovery chamber 31 through the filter 12 by means of the fan 11 flows through the punched holes 31b into a space outwardly of the inner shutter 21a of the decomposing shutter 21a, the system as a whole can be installed in a sufficiently reduced space for installation and, also, the recovery chamber 31 can be kept clean. It is to be noted that one of the cleansing of the retainer 32a and the drying of the substance to be measured can be performed prior to the other as desired or the both may be performed in parallel to each other, provided that they are performed after the retainer 32a has been retracted away from the position immediately above the solution 4 which has recovered the substance to be measured.

Subsequently, as shown in FIG. 1, the transport apparatus 50 transports the substrate 1, which has recovered the substance 2 to be measured, towards the cassette 47 within a delivery chamber of the X-ray fluorescence spectrometer 40. During this transport, the shutter 31a of the sample recovery apparatus 30 is automatically opened and closed. The X-ray fluorescence spectrometer 40, after the substrate 1 has been transported to the sample table 41 by the transport means 46, performs a total reflection X-ray fluorescence analysis. After the analysis, the substrate 1 is transported by the transport means 46 towards the cassette 47 within the delivery chamber and is then transported by the transport apparatus 50 towards the initial cassette 3 placed on the cassette support 5. It is to be noted that if during the initial analysis of the substrate 1, recovery of the next succeeding substrate and decomposition of the succeeding substrate after next are performed simultaneously, the overall preprocessing and the analyzing work can be quickly accomplished.

While the foregoing is an explanation of the spectrometric system under the VPD (vapor phase decomposition) mode, the operation of the spectrometric system under the VPT (vapor phase treatment) mode will now be described. Since under this VPT mode no recovery of the substance to be measured is carried out by the sample recovery apparatus 30, the substance to be measured is not concentrated and the sensitivity of the analysis will not increase so much as that under the VPD mode, but a distribution of the substance to be measured on the substrate can be ascertained. Also, even under the VPT mode, the substance to be measured can be transformed into finely divided particles as it is dried after having been dissolved by the vapor phase decomposition apparatus 20 in contact with hydrogen fluoride and, accordingly, the sensitivity during the total reflection X-ray fluorescence analysis can be increased.

The operation of the spectrometric system under the VPT mode is similar to that under the VPD mode so far as the process is concerned to a stage, in which within the vapor phase decomposition apparatus 20 shown in FIG. 2, the decomposing chamber 21 is evacuated while being supplied with nitrogen by the droplet drying means 24, with the hydrogen fluoride being purged, and the droplets formed on the substrate 1 are dried. Under this VPT mode, subsequent to the drying, the transport apparatus 50 transports the substrate 1, then retaining the substance 2 to be measured, towards the cassette 47 (FIG. 1) within the delivery chamber of the X-ray fluorescence spectrometer 40. At the time of this transport, the shutters 21a and 27 of the vapor phase decomposition apparatus 20 is automatically opened and closed. Thereafter, analysis by the X-ray fluorescence spectrometer 40 and the transport of the substrate 1 back to the initial cassette 3 by the transport apparatus 50 are sequentially carried out in a manner similar to those under the VPD mode.

Under the TXRF mode, the vapor phase decomposition as well is not performed by the vapor phase decomposition apparatus 20, that is, the preprocessing by the sample pre-treatment apparatus 10 is not performed. This corresponds to the substrate (sample) 1 that does not require the preprocessing and, under this mode, the transport apparatus 50 transports the substrate 1 from the cassette 3, placed on the cassette support 5, towards the cassette 47 within the delivery chamber of the X-ray fluorescence spectrometer 40. Thereafter, analysis by the X-ray fluorescence spectrometer 50 and transport of the substrate 1 back to the initial cassette 3 by the transport apparatus 50 are performed sequentially in a manner similar to those under the VPD mode. In other words, the spectrometric system functions as the standard total reflection X-ray fluorescence spectrometer.

Other than those described above, where no oxide film is formed on the substrate 1 and no dissolution of the film is required, it is possible to set under a DADD (direct acid droplet decomposition) mode under which during the sample preprocessing only recovery of the substance to be measured is carried out by the sample recovery apparatus 30. Under this DADD mode, the transport apparatus 50 transports the substrate 1 from the cassette 3 placed on the cassette support 5 towards the recovery chamber 31 of the sample recovery apparatus 30. Subsequently, recovery of the substance to be measured, cleansing of the retainer 32a and drying of the substance to be measured by the sample recovery apparatus 30, transport of the substrate 1 by the transport apparatus 50 towards the cassette 47 within the delivery chamber of the X-ray fluorescence apparatus 40, analysis by the X-ray fluorescence spectrometer 40, and transport of the substrate 1 by the transport apparatus 50 back to the initial cassette 3 are sequentially performed in a manner similar to those under the VPD mode.

While the spectrometric system shown and described in connection with the preferred embodiment of the present invention has been described as provided with the sample pre-treatment apparatus 10 including the vapor phase decomposition apparatus 20 and the sample recovery apparatus 30, it may suffice for the sample pre-treatment apparatus 10 to include either one of the vapor phase decomposition apparatus 20 and the sample recovery apparatus 30. Where the sample pre-treatment apparatus 10 includes only the vapor phase decomposition apparatus 20, it can operate under any one of the VPT and TXRF modes, whereas if the sample pre-treatment apparatus 10 includes only the sample recovery apparatus 30, it can operate under any one of the DADD and TXRF modes.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. An X-ray fluorescence spectrometric system which comprises:

a vapor phase decomposition apparatus operable to retain on a surface of a substrate a substance to be measured that is found on the surface of the substrate or a substance to be measured that is found on a surface of a film formed on the surface of the substrate or within the film, after such substance has been dissolved by a reactive gas and has subsequently been dried, in a decomposing chamber;

a sample recovery apparatus operable to drop a solution on the substrate having the surface on which the substance to be measures exists, to move the solution on the substrate surface while being retained by a retainer, and to retain the substance to be measured on the substrate surface after having been recovered in the solution and then dried, in a recovery chamber that is disposed above the decomposing chamber;

an X-ray fluorescence spectrometer operable to measure intensities of fluorescent X-rays emitted from the substance to be measured that is retained on the substrate by the vapor phase decomposition apparatus or the sample recovery apparatus, when such substance is irradiated by primary X-rays;

a transport apparatus operable to transport the substrate from the decomposing chamber towards the X-ray fluorescence spectrometer, to transport the substrate from the decomposing chamber towards the recovery chamber and to transport the substrate from the recovery chamber towards the X-ray fluorescence spectrometer; and a control apparatus for controlling the vapor phase decomposition apparatus, the sample recovery apparatus, the X-ray fluorescence spectrometer and the transport apparatus.

2. The X-ray fluorescence spectrometric system as claimed in claim 1, wherein the vapor phase decomposition apparatus includes a decomposing chamber cleansing means for flushing a cleansing liquid into the decomposing chamber for cleansing.

3. The X-ray fluorescence spectrometric system as claimed in claim 1, wherein the vapor phase decomposition apparatus includes a heating means for heating a gas to be introduced into the decomposing chamber.

4. The X-ray fluorescence spectrometric system as claimed in claim 1, wherein the vapor phase decomposition apparatus includes a substrate support having a downwardly narrowed taper formed with an inner periphery thereof so that the substrate can be placed at a predetermined position within the decomposing chamber.

5. The X-ray fluorescence spectrometric system as claimed in claim 1, wherein the sample recovery apparatus includes a retainer cleansing means for cleansing the retainer with a cleansing liquid.

6. The X-ray fluorescence spectrometric system as claimed in claim 1, wherein the sample recovery apparatus includes a rotary table for rotating the substrate in a horizontal plane when the substance to be measured that has been recovered in the solution is dried.

7. A program for enabling the control apparatus, included in the X-ray fluorescence spectrometric system as defined in claim 1, to perform one of VPD, VPT and TXRF modes according to a selection made by an operator, wherein: in the VPD mode;

the transport apparatus is caused to transport the substrate from a predetermined delivery position towards the decomposing chamber;

the vapor phase decomposition apparatus is caused to introduce the reactive gas into the decomposing chamber;

the transport apparatus is caused to transport the substrate towards the recovery chamber;

the sample recovery apparatus is caused to drop the solution on the substrate;

the sample recovery apparatus is caused to move the solution on the substrate surface while being retained by the retainer, and to recover the substance to be measured in the solution the sample recovery apparatus is caused to dry the substance to be measured;

the transport apparatus is caused to transport the substrate towards the X-ray fluorescence spectrometer;

the X-ray fluorescence spectrometer is caused to measure intensities of fluorescent X-rays emitted from the substance to be measured in response to irradiation thereof with primary X-rays; and the transport apparatus is caused to transport the substrate back towards the delivery position; In the VPT mode:

the transport apparatus is caused to transport the substrate from the predetermined delivery position towards the decomposing chamber;

the vapor phase decomposition apparatus is caused to introduce the reactive gas into the decomposing chamber;

the transport apparatus is caused to transport the substrate towards the X-ray fluorescence spectrometer;

the X-ray fluorescence spectrometer is caused to measure intensities of fluorescent X-rays emitted from the substance to be measured in response to irradiation thereof with primary X-rays; and the transport apparatus is caused to transport the substrate towards the delivery position; and In the TXRF mode:

the transport apparatus is caused to transport the substrate from the predetermined delivery position towards the X-ray fluorescence spectrometer;

the X-ray fluorescence spectrometer is caused to measure intensities of fluorescent X-rays emitted from the substance to be measured in response to irradiation thereof with primary X-rays; and the transport apparatus is caused to transport the substrate towards the delivery position.

8. An X-ray fluorescence spectrometric system which comprises:

a vapor phase decomposition apparatus operable to dissolve a substance to be measured that is found on a surface of a substrate or a substance to be measured that is found on a surface of a film formed on the surface of the substrate or within the film by a reactive gas in a decomposing chamber;

a sample recovery apparatus operable to drop a solution on the substrate having the surface on which the substance to be measures exists, to move tile solution on the substrate surface while being retained by a retainer, and to retain the substance to be measured on the substrate surface after having been recovered in the solution and then dried, in a recovery chamber;

an X-ray fluorescence spectrometer, including a transport means operable to transport the substrate between a cassette within a delivery chamber and a sample table, operable to measure intensifies of fluorescent X-rays emitted from the substance to be measured that is retained on the substrate by the sample recovery apparatus, when such substance is irradiated by primary X-rays;

a transport apparatus operable to transport the substrate from the decomposing chamber towards the recovery chamber and to transport the substrate from the recovery chamber towards the cassette within the delivery chamber of the X-ray fluorescence spectrometer; and a control apparatus for controlling the vapor phase decomposition apparatus, the sample recovery apparatus, the X-ray fluorescence spectrometer and the transport apparatus.

9. An X-ray fluorescence spectrometric system which comprises:

a vapor phase decomposition apparatus operable to dissolve a substance to be measured that is found on a surface of a substrate or a substance to be measured that is found on a surface of a film formed on the surface of the substrate or within the film by a reactive gas; a sample recovery apparatus operable to drop a solution on the substrate having the surface on which the substance to be measures exists, to move the solution on the substrate surface while being retained by a retainer, and to retain the substance to be measured on the substrate surface after having been recovered in the solution and then dried;

an X-ray fluorescence spectrometer, including a transport means operable to transport the substrate between a cassette within a delivery chamber and a sample table, operable to measure intensities of fluorescent X-rays emitted from the substance to be measured that is retained on the substrate by the sample recovery apparatus, when, such substance is irradiated by primary X-rays;

a transport apparatus operable to transport the substrate from the vapor phase decomposition apparatus towards the sample recovery apparatus and to transport the substrate from the sample recovery apparatus towards the cassette within the delivery chamber of the X-ray fluorescence spectrometer; and a control apparatus for controlling the vapor phase decomposition apparatus, the sample recovery apparatus, the X-ray fluorescence spectrometer and the transport apparatus.

\* \* \* \* \*